United States Patent [19]

Hanson et al.

[11] Patent Number: 5,075,229
[45] Date of Patent: Dec. 24, 1991

[54] DIETARY AND HORMONAL REGULATION OF EXPRESSION OF EXOGENOUS GENES IN TRANSGENIC ANIMALS UNDER CONTROL OF THE PROMOTER OF THE GENE FOR PHOSPHOENOLPYRUVATE CARABOXYKINASE

[75] Inventors: Richard W. Hanson; Mary McGrane, both of Cleveland Hghts, Ohio; Jay Short, Encinitas, Calif.; Maria Hatzoglou, Cleveland Hghts, Ohio

[73] Assignee: Ohio University Edison Animal Biotechnology Center, Athens, Ohio

[21] Appl. No.: 205,776

[22] Filed: Jun. 13, 1988

Related U.S. Application Data

[63] Continuation-in-part of Ser. No. 62,654, Jun. 16, 1987, abandoned.

[51] Int. Cl.⁵ .................. C12N 15/00; A61K 48/00
[52] U.S. Cl. ............................. 435/172.3; 514/44; 800/2; 800/DIG. 2; 935/62; 935/111
[58] Field of Search .............. 800/2; 435/68, 172.3, 435/240.2, 320, 317.1; 935/27, 32, 53, 57, 62, 111; 514/44

[56] References Cited

U.S. PATENT DOCUMENTS 4,579,821  4/1986  Palmiter et al. .................. 435/172.3
4,736,866  4/1988  Leder et al. ............................ 800/1

OTHER PUBLICATIONS

Ornitz et al., Nature 313: 600–602 (1985).
Hursar et al., Proc. Natl. Acad. Sci. 82: 8587–8591 (1985).
Wilmut et al., New Scientist, Jul. 7, 1988, pp. 56–59.
Van Brunt, Biotechnology 6(10): 1149–1154 (1988).
Weiss et al., RNA Tumor Viruses: Molecular Biology of Tumor Viruses, 2d Ed., Table 2S.1, "Retroviruses", Cold Spring Harbor, 1985.
Hatzoglou et al., Hepatic Gene Transfer in Animals using Retroviruses . . . , The Journal of Biological Chemistry, vol. 265, No. 28, pp. 17285–17293, Oct. 1990.
Wynshaw-Borris et al. (I), J. Biol. Chem. 261(21): 9714–9720 (1986).
Wynshaw-Borris et al. (II), J. Biol. Chem. 259(19): 12161–12169 (1984).
Andres et al. (I), Proc. Natl. Acad. Sci. 84: 1299–1303 (1987).
Andres et al. (II), Experientia 42: 673 (1986).

*Primary Examiner*—Elizabeth C. Weimar
*Assistant Examiner*—Jasemine C. Chambers
*Attorney, Agent, or Firm*—Iver P. Cooper

[57] ABSTRACT

A transgenic animal is constructed in which one or more cells contain a promoter to the gene for cytosolic PEPCK operably linked to a non-PEPCK gene of interest. Expression of this gene is controlled by modifying the protein and carbohydrate components of the animal's diet, or by direct hormonal regulation. The PEPCK promoter is induced by high protein and inhibited by high carbohydrate, or more directly by cAMP and insulin. The linked gene is expressed essentially only after bith and essentially only in particular tissues. The PEPCK promoter has a extremely high promoter strength.

2 Claims, 12 Drawing Sheets

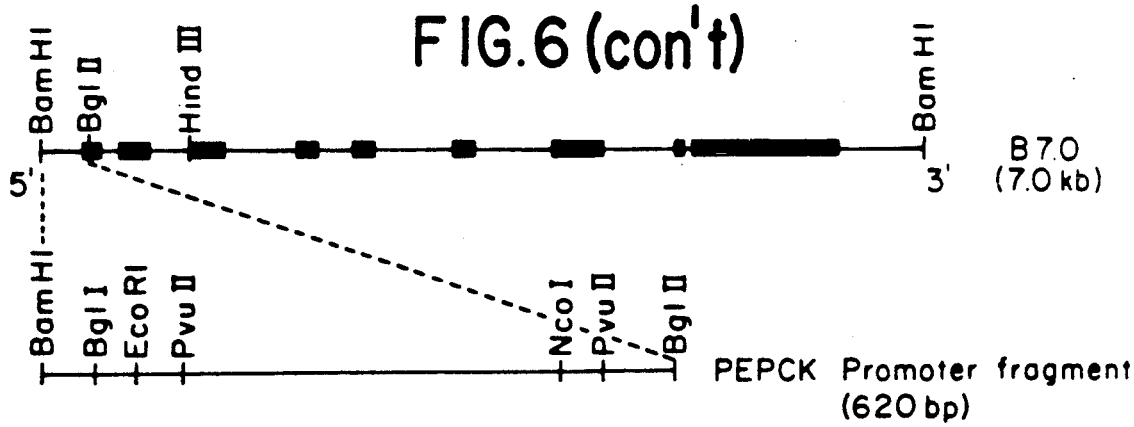

FIG.6 (con't)

```
-548                                                    -500
   GGATCCAGCA  GACACCTAGT  GGGGTAACAC  ACCCCAGCCA  ACTCGGCTGT
   ‾‾‾‾‾‾
   BAM HI
   TGCAGACTTT  GTCTAGAAGT  TTCACGTCTC  AGAGCTGAAT  TCCCTTCTCA
                                                        -400
   TGACCTTTGG  CCGTGGGAGT  GACACCTCAC  AGCTGTGGTG  TTTTGACAAC

CAGCAGCCAC  TGGCACACAA  AATGTGCAGC  CAGCAGCATA  TGAAGTCCAA
                                                        -300
   GAGGCGTCCC  GGCCAGCCCT  GTCCTTGACC  CCCACCTGAC  AATTAAGGCA

AGAGCCCTAT  AGTTTGCATC  AGCAACAGTC  ACGGTCAAAG  TTTAGTCAAT
                                                  ‾‾‾‾‾  ‾‾‾‾‾‾‾‾‾‾
                                                        -200
   CAAACGTTGT  GTAAGGACTC  AACTATGGCT  GACACGGGGG  CCTGAGGCTC

CCAACATTCA  TTAACAACAG  CAAGTTCAAT  CATTATCTCC  CCAAAGTTTA
                                                        -100
   TTGTGTTAGG  TCAGTTCCAA  ACCGTGCTGA  CCATGGCTAT  GATCCAAAGG
                                        ‾‾‾‾‾‾
                                        Nco I
   CCGGCCCCTT  ACGTCAGAGG  CGAGCCTCCA  GGTCCAGCTG  AGGGGCAGGG
                                                        -1+1
   CTGTCCTCCC  TTCTG TATAC . TATTTAAA GC  GAGGAGGGCT  AGCTACCAAG

CACGGTTGGC  CTTCCCTCTG  GGAACACACC  CTTGGCCAAC  AGGGGAAAGC
                      +73
   CGGCGAGACG  CTCTGAGATCT
                ‾‾‾‾‾‾‾
                BGL II
```

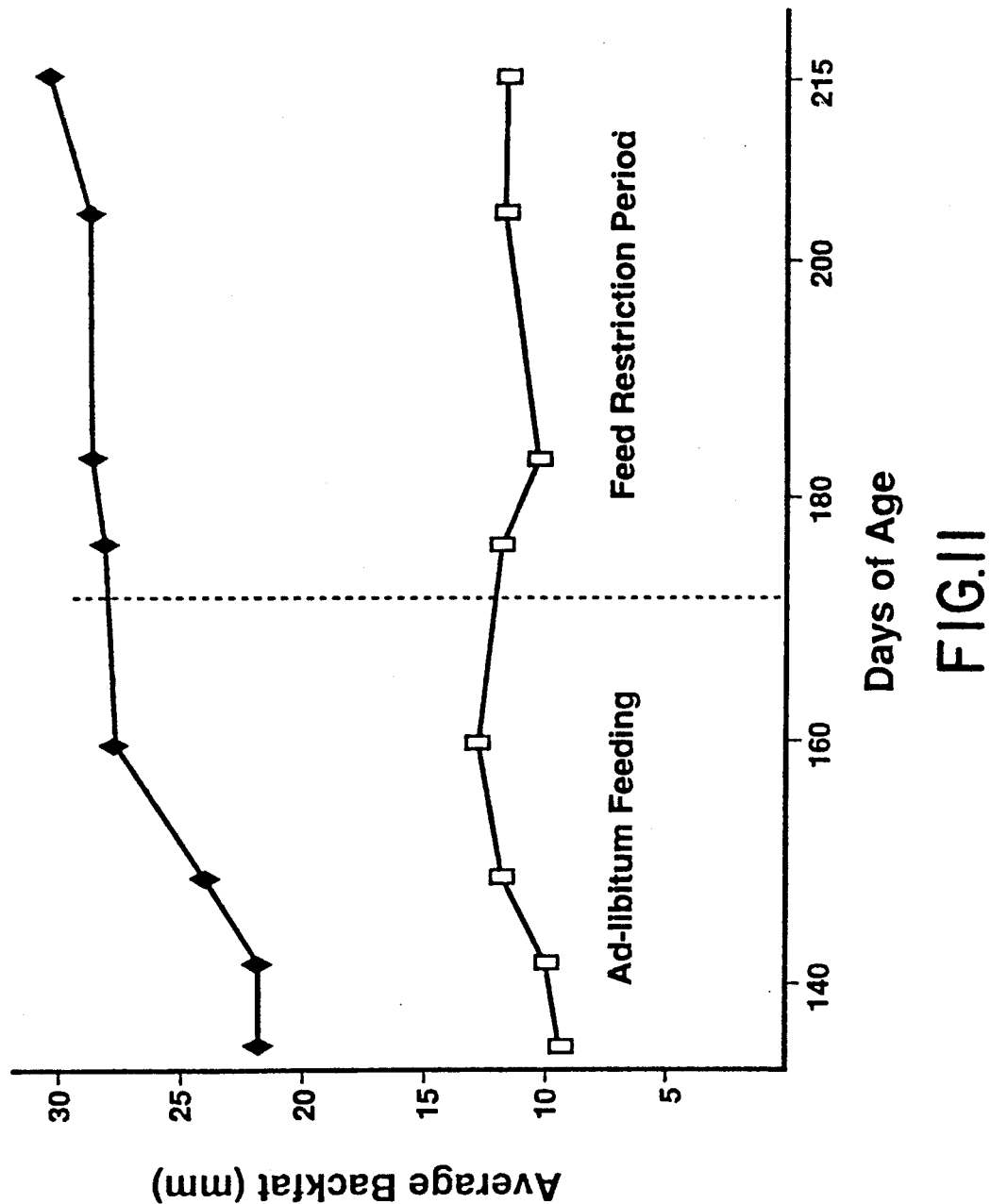

DIETARY AND HORMONAL REGULATION OF EXPRESSION OF EXOGENOUS GENES IN TRANSGENIC ANIMALS UNDER CONTROL OF THE PROMOTER OF THE GENE FOR PHOSPHOENOLPYRUVATE CARBOXYKINASE

RELATED APPLICATIONS

This application is a continuation-in-part of Ser. No. 07/62,654, filed Jun. 16, 1987, now abandoned, incorporated by reference herein. Priority is claimed pursuant to 35 U.S.C. 120.

BACKGROUND OF THE INVENTION

1. Field of the Invention

The present invention relates to the control of the expression of exogenous genes in transgenic animals and in tissue culture cells.

2. Information Disclosure Statement

In agriculture, it is often desirable that an animal have a particular trait. Traditionally, this was accomplished by breeding for the trait. Breeding, unfortunately, has many disadvantages. It may require many generations to fix a desired trait in an animal line. When the bred animals finally acquire that trait, they may also have acquired other, undesired traits. There is no guarantee that a particular individual will acquire the desired trait.

Consequently, a more controlled means of manipulating the phenotype of an animal was sought. The development of recombinant DNA technology offered a possible route to achieving this goal. Theoretically, if a trait was associated with a particular gene that an animal lacked, the gene could be introduced into the animal, thereby modifying its phenotype to include that trait. Of course, there were many hurdles to be surmounted. The genes associated with a particular trait had to be identified and isolated. Suitable regulatory sequences had to be functionally linked to these genes so that they would properly express the trait. The resulting units had to be stably introduced into the cells of the recipient animal. Then, and only then, could the "transgene" function as intended.

The transgene may be expressed in a transgenic animal under the control of a promoter/regulatory domain of choice. The promoter/regulatory domain determines whether the gene is expressed constitutively (at a constant rate and constant level) or whether it is silent or induced depending upon different environmental stimuli. The cytosolic phosphoenolpyruvate carboxykinase (PEPCK) (EC 4.1.1.32) promoter is an example of the latter type of promoter/regulatory domain.

If the exogenous gene is constitutively expressed, the constant expression of the corresponding protein product of this gene may have undesirable effects on the host animal. This could be especially deleterious during embryogenesis when the programmed expression of genes is necessary for orderly development. Consequently, it is desirable to control expression of the gene by means of an inducible or repressible promoter. Additionally, it is desirable to use a promoter which is controllably responsive to changes in diet, since these changes are readily affected.

Many inducible promoters are known. One such promoter regulates the expression of the gene for the cytosolic form of PEPCK, a gluconeogenic enzyme discovered in 1954 by Utter and Kurahashi. This enzyme has a high specific activity in liver, kidney cortex, and white adipose tissue and in lesser levels in lung and jejunum. Hanson and Garber, Am. J. Clin. Nutrition, 25:1010 (1972); Utter and Kurahashi, J. Biol. Chem., 207:287 (1954). There are both cytosolic and mitochondrial forms of PEPCK encoded by different nuclear genes. There are species-specific variations in the expression of both PEPCK forms. The genes for the cytosolic form of this enzyme in the rat and the chicken have been isolated and characterized. Yoo-Warren, et al., PNAS 80:3656–60(1983) (rat) and Hod, Yoo-Warren and Hanson, J. Biol. Chem., 259:15609–15614 (1984) (chicken).

Gluconeogenesis is a process by which non-hexose precursors are converted to glucose to support glucose homeostasis in all vertebrate animals. It occurs only in the liver and kidney cortex. Gluconeogenesis from lactate (Cori cycle) involves 13 enzymes and includes several reactions which also play a role in the citric acid cycle, or in glycolysis, as well as other reactions which are specific for this process. The major precursors for glucose synthesis, in addition to lactic acid, are pyruvic acid, amino acids (such as alanine or glutamine) and glycerol. The pathway is stimulated during periods of starvation or during diabetes, and is depressed by dietary carbohydrate. The major hormonal controls of gluconeogenesis are glucagon (acting via cAMP), which stimulates gluconeogenesis, and insulin, which represses the synthesis of glucose. It is important to distinguish the de novo synthesis of glucose (gluconeogenesis) from glycogenolysis, the breakdown of preformed glucose which is stored in the liver and muscle as glycogen. PEPCK is the first committed step in the gluconeogenic pathway and is the pace-setting enzyme in this process. The marked inducibility of the gene for this enzyme reflects the important regulatory position that PEPCK plays in maintaining glucose homeostasis.

In the liver, PEPCK is induced by glucagon, epinephrine, norepinephrine, glucocorticoids, and thyroxine, and deinduced by insulin. In the kidney, acidosis or glucocorticoids elevate PEPCK expression, while alkalosis inhibits PEPCK synthesis. Finally, in adipose tissue, norepinephrine and epinephrine boost PEPCK levels while insulin and glucocorticoids decrease the levels of the enzyme. See Table I, "Factors that alter the levels of PEPCK in rat tissues", in Tilghman, et al., "Hormonal Regulation of Phosphoenolpyruvate Carboxykinase (GTP) in Mammalian Tissues", published as Chapter 2 of Gluconeogenesis: Its Regulation in Mammalian Species, Hanson and Mehlman, eds., (1976).

Hormonal regulation of PEPCK gene expression is tissue-specific. (See Hanson and Mehlman, cited above). However, there is a paucity of information on the sequences responsible for the tissue-specific expression of this gene or for the differences in response to hormones in tissues such as liver and adipose tissue.

Dietary effects on the activity of PEPCK are known. Starvation for 24 hours produces a threefold increase in enzyme activity, which is reversed by a diet high in carbohydrate (e.g., glucose, fructose, and glycerol) or exacerbated by refeeding with a high protein diet. Shrago, et al., J. Biol. Chem., 238:3188 (1963). According to Peret and Chanez, J. Nutrition, 106:103(1976), a high protein diet induced the activity of hepatic PEPCK in mammals (rats), and the activity increased as the protein content of the diet was increased. Pyruvate carboxylase, another gluconeogenic enzyme, was not affected in this manner.

In mammals, the maternal blood supply is cut off at birth, resulting in a transient neonatal hypoglycemia.

This results in a fall in the concentration of plasma insulin and a rise in the level of glucagon. This causes an increase in the concentration of hepatic cAMP, which induces the initial expression of PEPCK. The appearance of this enzyme completes the gluconeogenic pathway, and hepatic gluconeogenesis is thereby initiated.

The sequence of the promoter naturally regulating expression of the gene encoding cytosolic PEPCK is given in FIG. 1 of Wynshaw-Boris, et al., J. Biol. Chem., 259:12161 (1984), and is incorporated by reference herein. The rate of transcription of the PEPCK gene in nuclei from the livers of animals induced by hormones is known to be high and is comparable to that reported for the heat-shock gene. See Table 1, in Meissner, et al. (1983), supra. Certain regulatory domains of the "PEPCK promoter" have been identified. Wynshaw-Boris, et al., J. Biol. Chem., 261:9714 (Jul. 25, 1986); Short, et al., J. Biol. Chem., 261:9721 (Jul. 25, 1986). The PEPCK promoter has been used to control expression of both the Herpes virus thymidine kinase (TK) gene and the amino-3'-glycosyl phosphotransferase (AGPT or neo resistance) gene in transfected hepatoma (FTO-2B) cells. Both TK and AGPT synthesis were responsive to cAMP and dexamethasone. Id.; Wynshaw-Boris, et al., BioTechniques, 4(2):104(1986).

Kawasaki, U.S. Pat. No. 4,599,311 advocates the use of yeast promoters which control genes coding for enzymes in the glycolytic pathway (hexokinase 1 and 2, phosphoglucose isomerase, phosphoglycerate kinase, triose phosphate isomerase, phosphoglycerate mutase, pyruvate kinase, phosphofructokinase, enolase, fructose 1, 6-diphosphate aldolase, glyceraldehyde 3-phosphate dehydrogenase, and glycolysis regulation protein). These are coupled to foreign genes and used to control expression of those genes in transformed yeast cells. Kawasaki refers in a general way to regulating the expression by choosing the appropriate nutrient medium. However, he is limited to yeast promoters and yeast cells for the expression of any recombinant gene and production of a given gene product. The gene products may also be inappropriately glycosylated due to the fact that they are secreted by yeast cells. Furthermore, the glycolytic yeast promoters cannot by used in intact animals and will not be expressed in organisms other than yeast.

Kingsman, U.S. Pat. No. 4,615,974 specifically used the yeast phosphoglycerate kinase (PGK) promoter, a glycolytic pathway promoter, to control alpha interferon expression in yeast. Production was induced by introducing glucose into the culture medium.

There is no discussion in either Kawasaki or Kingsman of using diet to control expression of an introduced gene in the cells of a whole animal, or of selecting a gene system which is active essentially only after birth.

Konrad, U.S. Pat. No. 4,499,188 relates to the expression of a heterologous gene in a transformed bacterial cell under TRP promoter control. The medium is initially rich in tryptophan, thereby repressing the gene. Bacterial growth consumes the tryptophan, eventually switching on the gene. The tro promoter is limited to use in prokaryotic cells.

Palmiter, U.S. Pat. No. 4,579,821 describes Herpes virus thymidine kinase (TK) gene expression in adult mice grown from embryos microinjected with a recombinant rDNA vector. This vector contains the TK gene operably linked to the mouse metalothionein-I (MT-I) promoter. This promoter is regulatable by administration of heavy metals such as cadmium or steroid hormones such as dexamethasone. The induction of this promoter or of the mouse MT-II promoter by feeding heavy metals to transgenic animals is inherently limited by considerations of acute and chronic toxicity and teratogenicity. Prolonged feeding of steroid hormones may also have adverse effects. Moreover, since the MT-I promoter, unlike the PEPCK promoter, is active during fetal development, fetal expression of the linked exogenous gene may have deleterious effects upon a transgenic fetus.

While the PEPCK promoter may be induced using dexamethasone, see Wynshaw-Boris, et al. (1986), it is substantially more responsive to hepatic cAMP than to glucocorticoids. Indeed, while liver PEPCK activity may be induced in an adrenalectomized animal by starvation, injection of dexamethasone into a well-fed, adrenalectomized animal does not induce PEPCK activity. Reshef, et al., J. Biol. Chem., 244:5577–81(1969).

The PEPCK promoter is more strongly and rapidly induced by cAMP than is the MT-1 promoter by dexamethasone. In addition, in transgenic animals, the expression of the PEPCK promoter is readily modulated by adjustment of the protein and carbohydrate content of the animal's diet.

There has been considerable interest in using recombinant DNA techniques to express bovine growth hormone or closely-related species, as evidenced by the following references:

Miller, EP Appl 47,600;
Rottman, EP Appl 67,026;
De Boer, EP Appl 75,444;
De Geeter, EP Appl 85,036;
Buell, EP Appl 103,395;
Rottman, EP Appl 112,012;
Aviv, EP Appl 131,843;
Hsiung, EP Appl 159,123;
Kopchick, EP Appl 161,640;
Krivi, EP Appl 193,515;
Aviv, GB 2,073,245; and
Fraser, U.S. Pat. No. 4,443,539.

Particular attention is drawn to Rottman, EP Appl 67,026, which discloses a deposited plasmid (PLG 23) bearing a cDNA copy of the bGH gene, and EP Appl 112,012, setting forth the nucleotide sequence of genomic BGH. None of these references suggest the use of the PEPCK promoter to control bGH expression.

SUMMARY OF THE INVENTION

We have found that the PEPCK promoter has special utility in the regulation of the expression of genes other than PEPCK in selected tissues of transgenic animals.

First, it may be controlled externally by changing the diet of the animals. Feeding an animal a diet high in protein and low in carbohydrate causes the secretion of glucagon and/or epinephrine. These two hormones raise the level of cAMP in target tissues, which in turn stimulates PEPCK promoter activity. As dietary carbohydrate is increased, insulin levels are raised, decreasing the expression of the PEPCK gene. Dietary manipulation is simpler, more economical, and less potentially harmful to the host animal than hormonal treatment.

Second, the PEPCK promoter is not induced significantly until immediately after birth. Thus, the developing fetus need not contend with the expression during development of the heterologous structural gene which is linked to the PEPCK promoter. In nature, PEPCK gene expression commences only after the maternal supply of glucose is cutoff by the severance of the umbilical cord. Our PEPCK-controlled genetic expression system thus has the advantage that the developing embryo and fetus are protected from the improper expression of the linked structural gene.

Third, a gene linked to the PEPCK promoter was observed to be expressed only in those cells which normally express high levels of PEPCK, i.e., the liver and kidney. We believe that this tissue specificity is imparted by the proximal 460 bp of the promoter.

Fourth, the PEPCK promoter, when induced, is characterized by a very high level of expression. According to Meisner et al., 1983, the transcription rate of PEPCK mRNA in the liver of starved rats was 3,500 ppm, as compared to 3,000 ppm for the heat shock gene of Drosophila, 270 ppm for bovine growth hormone mRNA in the bovine anterior pituitary, and 260 ppm for metallothionein mRNA in the liver of steroid-treated rats. The mRNA for PEPCK has a half-life of about 30 minutes, so mRNA levels are largely dependent on the transcription rate.

While the PEPCK promoter has particular utility in controlling the expression of exogenous genes in transgenic animals, it also is useful for controlling the expression of genes by eukaryotic cells in cell culture. Here, its prime advantages are its ready inducibility and de-inducibility and high promoter strength.

For in vitro expression of an exogenous gene, the PEPCK promoter is preferably induced by cAMP, and de-induced by insulin. Thus, cAMP and insulin offer a paired inducer-repressor system for finely controlling gene expression.

Other advantages of the present invention will be apparent after review of the specification, drawings, and claims. The claims are hereby incorporated by reference into the specification as a list of the preferred embodiments.

BRIEF DESCRIPTION OF THE DRAWINGS

FIG. 11 Comparisons between a PEPCK/bGH transgenic pig and its control littermate Change in backfat over time for transgenic pig #11(open squares) and control pig #12 (black diamonds). Backfat depth was measured ultrasonically at the first rib, last rib and last lumbar vertebra and the values averaged.

DETAILED DESCRIPTION OF THE INVENTION

Figure 1:
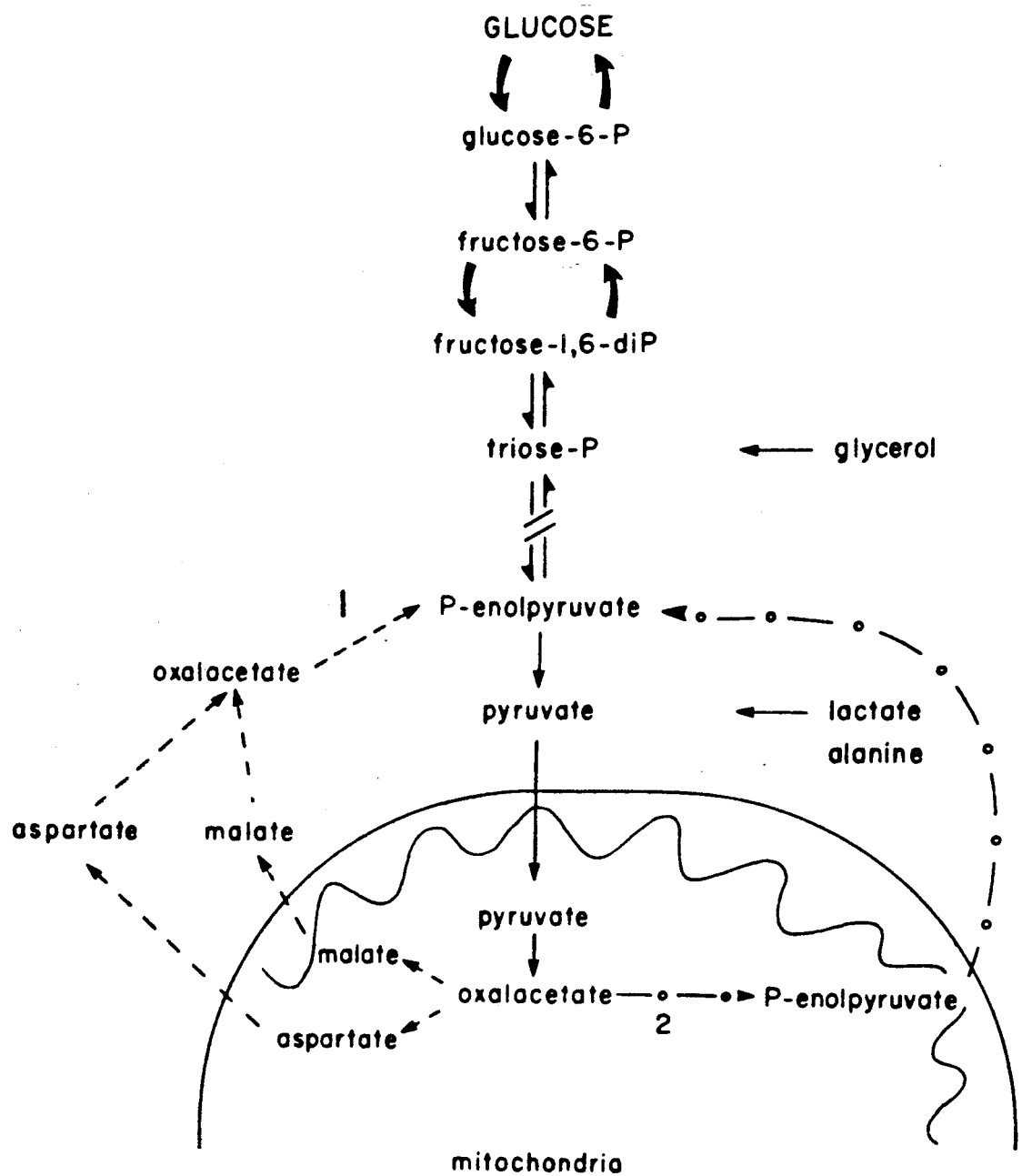
FIG. 1. Diagram of the gluconeogenic pathway showing the position of the cytosolic (1) and mitochondrial (2) forms of the PEPCK enzyme.

The term "animal" is used herein to include all vertebrate animals, including humans. It also includes an individual animal in all stages of development, including embryonic and fetal stages.

For the purpose of the appended claims, a "transgenic animal" is any animal containing one or more cells bearing genetic information received, directly or indirectly, by deliberate genetic manipulation at a subcellular level, such as by microinjection or infection with recombinant virus. The term is not intended to encompass classical cross-breeding or in vitro fertilization, but rather is directed to encompass animals in which one or more cells bear a recombinant DNA molecule. This molecule may be integrated within a chromosome, or it may be extrachromosomally replicating DNA. The term "germ cell line transgenic animal" refers to a transgenic animal in which the genetic information was introduced into a germ line cell, thereby conferring the ability to transfer the information to offspring. If such offspring in fact possess some or all of that information then they, too, are transgenic animals.

The information may be foreign to the species of animal to which the recipient belongs, e.g., a bovine growth hormone gene in a rat cell. It may be foreign only to the particular individual recipient, such as a gene encoding an enzyme that has been introduced into an individual who congenitally lacks the ability to synthesize that enzyme. Or it may be genetic information already possessed by the recipient. In the last case, the introduced gene may be more efficiently expressed, or expressed under conditions different than the native gene, as a result of the manipulation.

Additionally, the term "PEPCK promoter", when used without gualification, shall include the promoters for the PEPCK gene of any animal genome, or their artificial equivalents, as well as modifications of same, which are responsive to cAMP and insulin. The term thus does not include the promoter of the gene encoding the mitochondrial isozyme of PEPCK.

While the PEPCK promoter is preferred because of its responsiveness to dietary control signals, the promoters of other genes which are expressed significantly only post-parturition (after birth) may be of value in controlling the expression of genes introduced into animals. One such promoter is that of the gene which codes for tyrosine aminotransferase. It will be understood that while it is desired that the promoter be selected so that the transgenic animal be essentially incapable of expression of the gene before birth, some expression may be tolerable. The nature of the gene will dictate whether its expression before birth at a particular level is acceptable or not. In the case of the native PEPCK promoter, two adult animals were found to express 2440 and 3432 milliunits (mU) per gram of liver, while fetuses expressed only 40–50 mU/g liver. Ballard and Hanson, Biochem. J., 104:866–871 (1967). Thus, the ratio of adult-to-fetal expression of enzyme activity was about 60:1. Preferably, the promoter of this invention will provide a ratio of adult-to-fetal expression of the linked gene of at least 10:1. Preferably, it will also have a signal strength of at least 1000 ppm, i.e., about four times the bGH or MT promoters.

Additionally, it is conceivable that one might use other promoters responsive to dietary signals. Such promoters might include those for the gene coding the NADP-malate dehydrogenase and fatty acid synthase. They are stimulated by dietary glucose (acting via insulin) and inhibited by glucagon.

The PEPCK promoter may be used to control the expression of any structural gene of interest, such as those encoding bovine growth hormone, adenosine deaminase, thyrotropin-releasing hormone, beta-globin; including oncogenes, and marker genes such as herpes virus' thymidine kinase gene and the bacterial transposon AGPT gene.

In the experimental example described herein, the PEPCK promoter was linked with the bovine growth hormone gene, but it will be understood that the invention is not limited to the PEPCK/bGH expression system.

The rationale for the use of PEPCK/bGH is severalfold. First, the expression of bGH is readily detectable in the serum of transgenic animals by radio immunoassay. Second, the expression of bGH phenotypically alters the transgenic animal so that it grows to a larger size than control animals that do not contain the PEPCK/bGH transgene. Third, with respect to application in agricultural animals, the expression of bGH under the control of an active promoter such as PEPCK, while increasing the size of the transgenic animal, may also increase the protein to fat ratio of these animals, thus changing its body composition. The usefulness of GH in altering body composition in livestock has been demonstrated. Currently, however, the only method for administering GH is injection directly into the animal. The availability of transgenic animals which contain the GH gene integrated in their genome, would be of considerable commercial importance.

Another example of the use of the PEPCK promoter to drive a linked transgene in a genetically modified animal would be to use a retroviral vector to introduce a chimeric gene containing the PEPCK promoter ligated to the thyroid releasing hormone (TRH) gene into the germ line of chickens. TRH is a growth factor. Injection of the protein into each chicken is laborious and expensive.

A detailed description of our experimental work with the PEPCK/bGH system follows, but it is intended to illustrate and not to limit the present invention.

The bovine growth hormone genomic sequence is known. A bGH genomic sequence insert was removed from a lambda Charon 28 clone of a bovine placental library. An Eco RI restriction digest removed a 4.3 kb sequence containing the entire structural gene, 1.7 kb of 5'-flanking sequence, and 400 bp of 3'-flanking sequence, and this was cloned into the unique Eco RI site of the commercially available plasmid pBR322. The resulting bGH transfer vector is publicly available. See Woychik, et al., Nucl. Acids Res., 10:7197 (1982).

The bGH gene, or other genes of interest, need not be of genomic origin. It may be a cDNA transcript, or it may be partially or wholly synthetic. References for techniques for cloning bGH are cited in the "Background" section.

Figure 6:
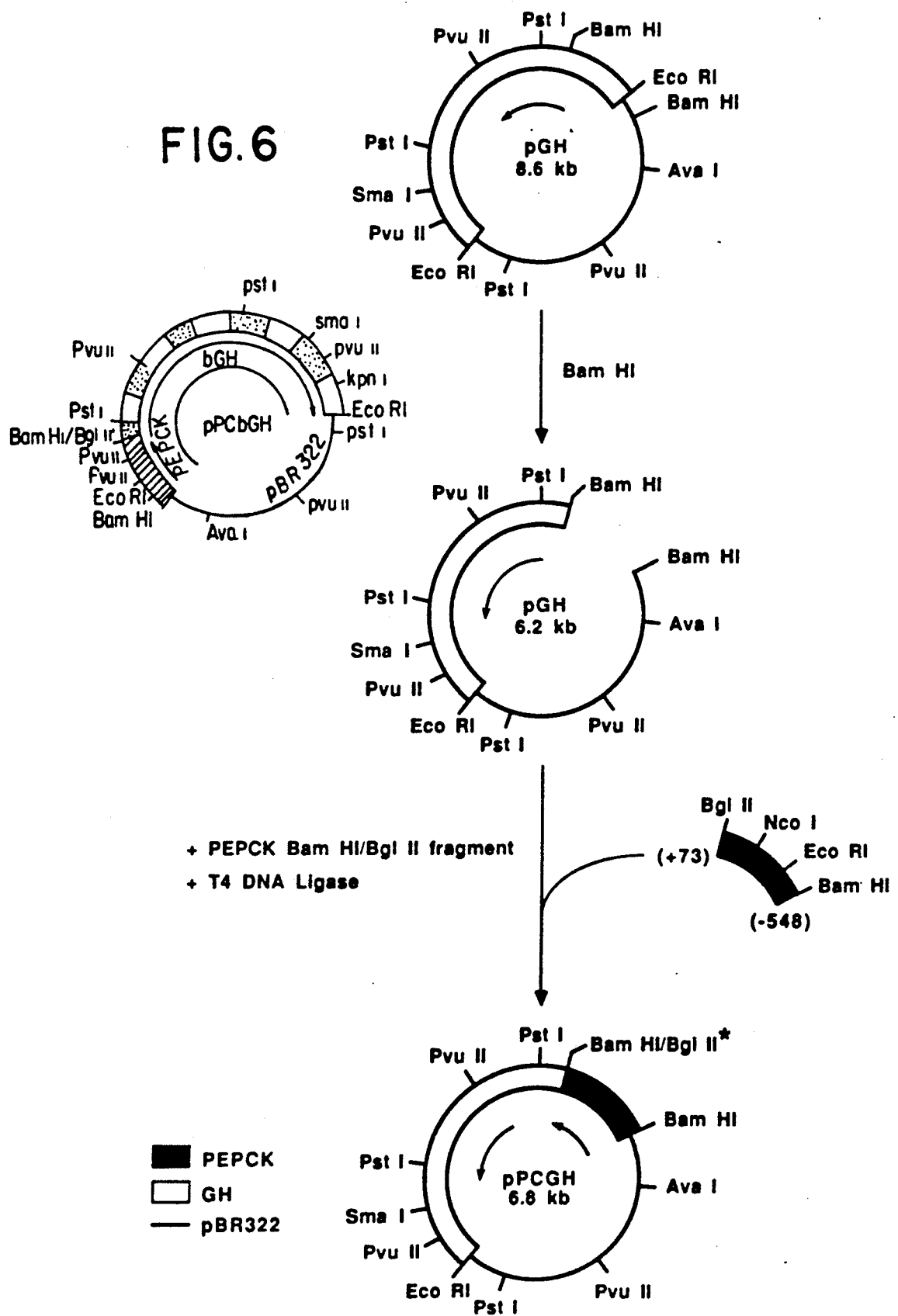
FIG. 6. Construction of pPCGH. A-548 to +73 fragment of the PEPCK promoter/gene is cloned into pGH to obtain pPCbGH.
Figure 7:
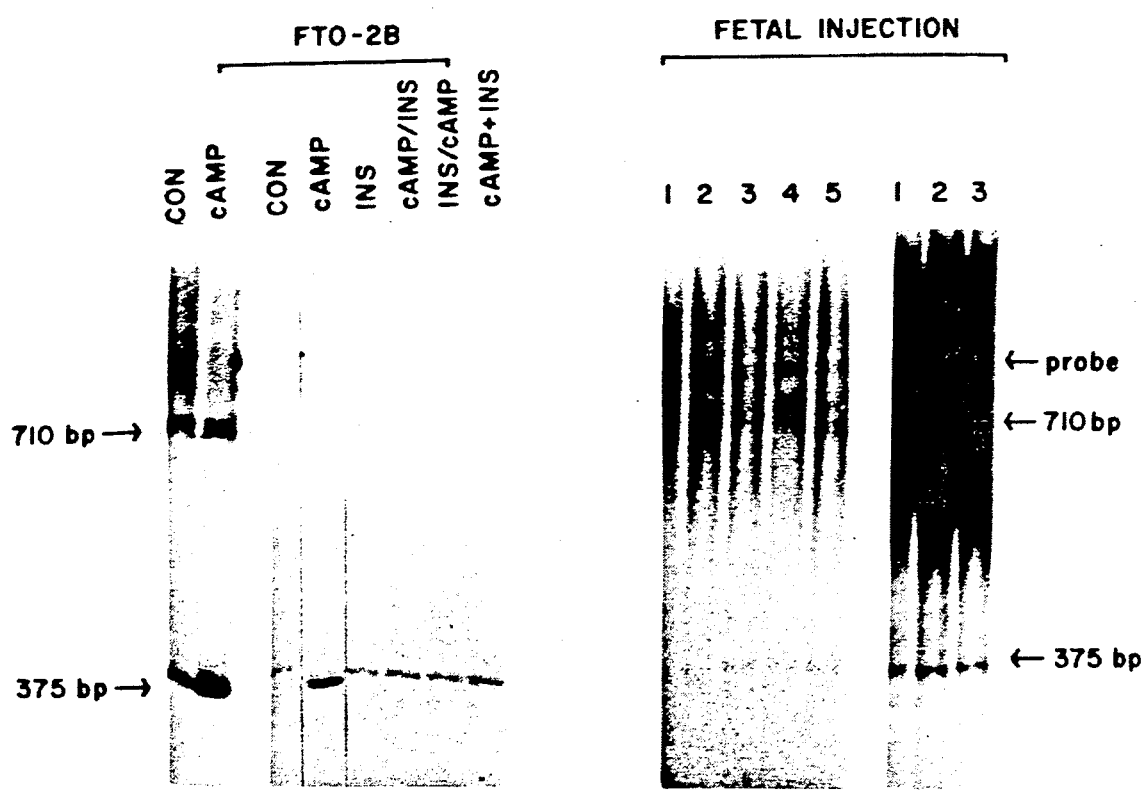
FIG. 7. Expression of a chimeric gene containing the PEPCK promoter ligated to the structural gene for AGPT or neo. Quantitative S1 nuclease mapping of the mRNA produced from a infectious retrovirus, pLJPCKneo, shown in FIG. 8, which was used to infect ITO-2B hepatoma cells, or injected into the peritoneal cavity of 19 day fetal rats. A Pvu I/Bgl II fragment of 1460 bp, which includes the Bgl II/EcoRI fragment (830 bp) from pLJPCKneo (FIG. 8) and 630 bp of pBR322 was end-labeled with [$P^{32}$] at the Bgl II site and hybridized to the total RNA extracted from the cells or liver. The 710 bp fragment is a transcript from the 5'LTR of the retrovirus (viral LTR RNA) and the 375 bp fragment is protected by a RNA transcript from the PEPCK promoter (PCK-neoRNA). The lanes were as follows: CON, no hormones; cAMP; INS, insulin; cAMP/INS; hormones added together; INS/cAMP, insulin added two hour before cAMP; cAMP +INS, insulin added 2 hours after cAMP. Fetal Injection: Lanes 1–5, RNA from the livers of 1 month old rats that had been injected as 19 day old fetus with pLJPCKneo in utero and administered cAMP (25 ng/kg body weight) by intraperitoneal injection 3 times at 20 minute intervals. The RNA was isolated and subjected to S1 nuclease mapping. Lane 1–3 on the right are longer exposures (48 hours) of the lanes on the left. All lanes contain 40 ug of total RNA isolated from the cells or from the liver of animals as indicated above.
Figure 7:
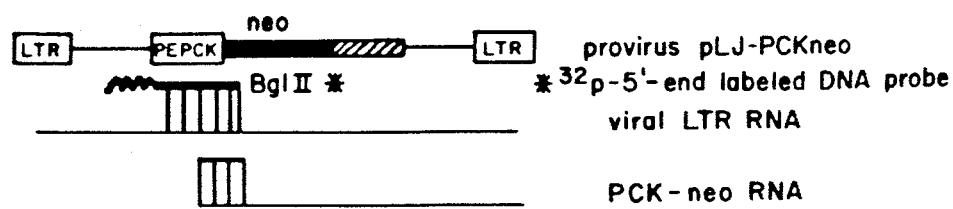
Figure 8:
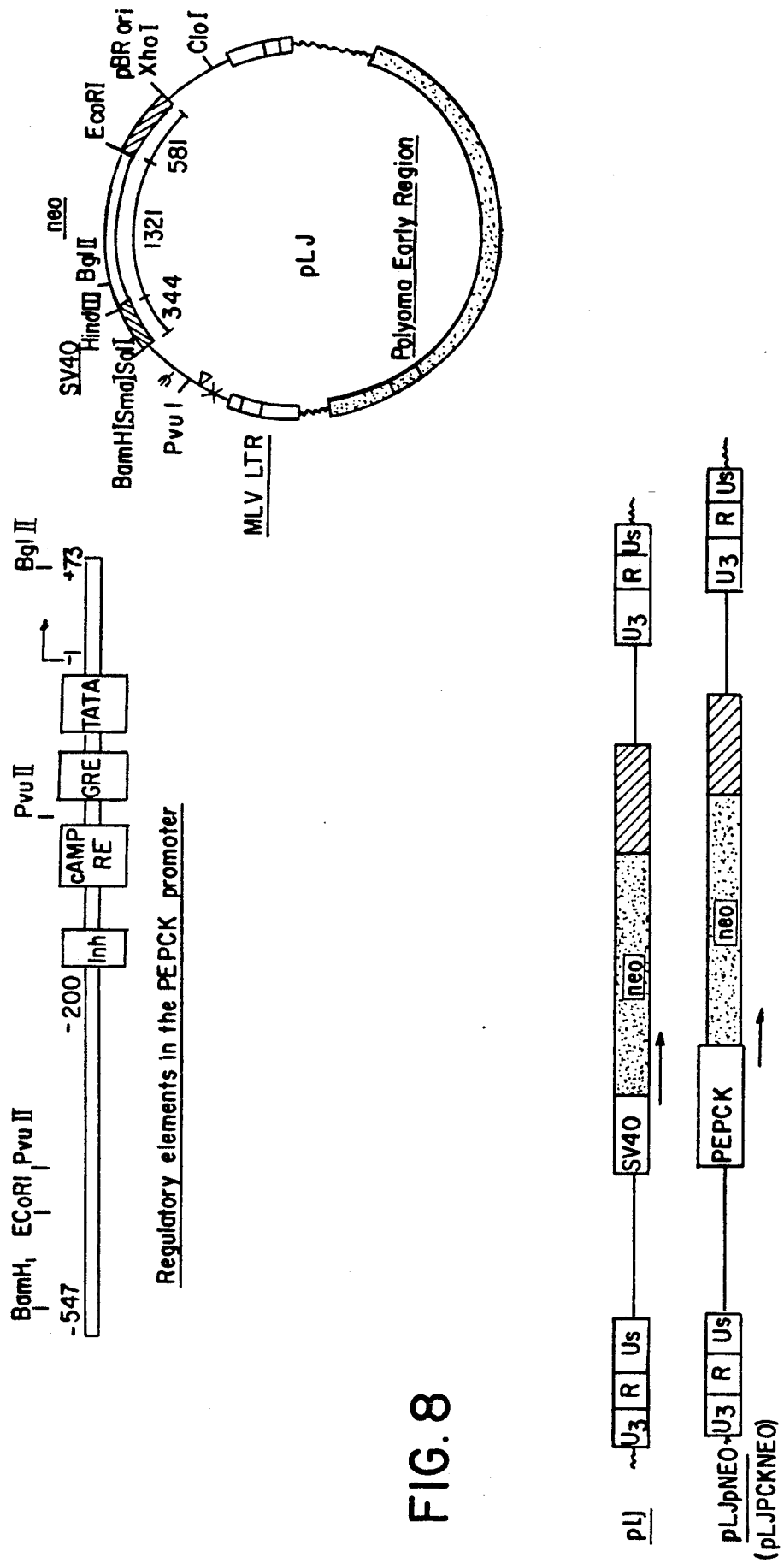
FIG. 8 Retroviral Vectors Containing the PEPCK Promoter Ligated to the AGPT or neo Structural Gene. A portion of the PEPCK promoter is shown as a Bam HI/Bgl II-fragment with the various regulatory elements indicated. The retroviral vector pLJ is shown in the right of the Figure as a circle. At the bottom is the retroviral vector pLJPCKneo containing the PEPCK promoter ligated to the neo structural gene and contained within the LTRs of the retroviral vector. The plasmid pLJPCKneo was used for the experiments described in FIG. 7.

The sequence of a functional portion of the natural rat liver (cytosolic) PEPCK promoter (−548 to −1) and of a part of the PEPCK structural gene (+1 to +73) is given in FIG. 6, and is based on Wynshaw-Boris, et al., (1984). As described in that article, this 621 bp Bam HI-Bgl II fragment has been cloned into the plasmid pOPF, operably linked to the thymidine kinase structural gene (pPCTK-6A). The plasmid pOPF also contains the SV40 enhancer, but this element does not diminish the hormonal response of the PEPCK promoter.

While we employed the promoter for the gene for cytosolic PEPCK from the rat, it is evident that other cytosolic PEPCK promoters may be advantageously used to control the expression of a gene of interest. The mitochondrial form of the PEPCK enzyme is constitutively expressed under the control of a different promoter and is encoded by a different gene. The promoter associated with the gene encoding the native mitochondrial form of PEPCK is not of great value in the present invention since it is not subject to the same acute regulation as the gene for the cytosolic form.

While we employed a functional fragment of the native promoter for the cytosolic form of PEPCK, deletion or substitution mutants of the native promoter may have advantages in specific situations. A series of 5'-deletion mutants are described in Short, et al., (1986). This and other articles cited in the "Background" section have characterized the different regulatory domains of the PEPCK promoter and therefore provide some guidance as to where to change the sequence. For example, a cAMP regulatory elements is believed to lie between −91 and −80. The −61 to −416 segment can act as a hormonally active enhancer. Wynshaw-Boris, et al., (1986).

In addition, consideration of the sequences of other glucocorticoid (metallothionein) and cAMP (preprosomatostatin, plasminogen activator, vasoactive intestinal polypeptide) responsive elements may also lead to the development of desirable non-native forms of the PEPCK promoter or to additional regulatory regions of DNA associated with the controlled expression of the PEPCK gene.

Returning to the experimental example, a Bam HI-Bam HI fragment was removed from the bGH-bearing plasmid, and replaced by the aforementioned 621 bp PEPCK promoter-bearing unit. The replaced DNA included the entire 5'-flanking sequence of the bGH gene, as is shown by the markings on the bGH sequence appearing in FIG. 6. The resultant fusion gene includes 73 bp of the first exon of the PEPCK structural gene linked at the Bgl II site to the start of the first exon of bGH. However, since the translation start site of PEPCK is further "downstream" than +73, there is no interference with the normal translation of the bGH gene-derived mRNA into active bGH.

The ligation of the PEPCK gene promoter to other genes may be accomplished by similar means, possibly including the use of other restriction enzymes and/or linker or adapter molecules. The basic considerations are that the PEPCK promoter remain functional, that the entire structural gene of interest be expressed, and that no portion of the PEPCK gene is expressed as a part of a fusion protein including the desired polypeptide.

At this point, we have a chimeric PEPCK promoter/bGH gene-bearing plasmid. Any art-recognized method may be used to prepare a transgenic animal bearing the desired expression system. In our experimental example, embryonic cells of the desired host animal were transformed by microinjection, and allowed to complete development and growth.

To prepare the chimeric gene for microinjection, the bacterial sequences were removed by Eco RI digestion. This also removed 87 bp of the PEPCK 5'-flanking sequence, but the promoter remained inducible by cAMP and by a high protein diet.

In a preferred embodiment, single cell embryos are flushed from the oviduct of superovulated C57BL6/SJL mice 14 hours after fertilization. The ova are washed with hyaluronidase to remove cumulus cells and transferred to a slide, in a salt medium containing lactate and pyruvate, for microinjection. Under a Leitz divert inverted microscope, an injector pipette containing approximately 1 pl of DNA solution (200 copies of the PEPCK/bGH gene) is inserted into the male pronucleus of the fertilized ovum and the DNA is injected (For a review of the technique see Hogan, B. Constantini, F and Lacy, E. "Manipulating the Mouse Embryo," Cold Spring Harbor Laboratory, 1986). The ova are incubated for 16 hours. After this incubation period, viable embryos are reimplanted in the oviducts of pseudopregnant mice. Wagner, et al., P.N.A.S. (USA) 78: 6376–80 (1981). These mice then gave birth to normal size liters of 6–10 pups.

Another method of preparing transgenic animals is by infection of pre-implantation embryos with retroviruses that contain a gene of interest or of therapeutic value. Through the use of recombinant DNA techniques, the retroviral genome can be manipulated to include an exogenous gene and exogenous promoter. The recombinant retroviral genome can be packaged within its viral capsid and used as viable infectious virus. Embryos at the single cell stage or later stages of development can be infected with the recombinant retrovirus and the provirus containing the exogenous gene will become integrated into the host genome as a single copy. Therefore, infection with recombinant retrovirus allows for the integration of an exogenous gene under the control of its own promoter or a heterologous promoter within the embryonic genome. Infected embryos can then be transferred to pseudopregnant female mice in the same manner that microinjected embryos are transferred, and the resultant offspring then assayed for the presence of the exogenous gene.

We have constructed both murine and avian retroviral vectors that contain the PEPCK promoter linked to the AGPT gene; these have been tested for expression by infection of fibroblast cells in culture. The PEPCK promoter is active within the provirus and high levels of PEPCK/AGPT mRNA have been detected in infected cells. Transcription is initiated at the proper start site and accurate hormonal regulation of transcription is observed. Therefore, the PEPCK promoter/regulatory domain will be very useful for this alternate method of production of transgenic animals.

It is not necessary to introduce the exogenous DNA into the animal at an early embryonic stage. The PEPCK promoter, linked to an appropriate structural gene and incorporated into a retroviral vector, may be used to infect cells of fetal animals during development. We have shown that the injection of a retrovirus into the peritoneal cavity of 19-day fetal animals (last trimester of development) results in the integration of the chimeric PEPCK-AGPT or neo gene into the chromosomes of the liver. While not all liver cells are infected, we can detect mRNA in the liver and the transcription of the gene is stimulated by cAMP. This procedure is effective, presumably because the liver is differentiating from a hemopoietic tissue to a hepatic tissue during this stage of development. This differentiation involves DNA replication and the infectious retrovirus then integrates into the liver cell genome. Since the retrovirus is a replication deficient virus, the animal will not produce further rounds of viral infection. This technique has potential for effectively introducing genes into animal tissues late in development, by a relatively non-invasive technique.

Yet another possibility is to introduce the vector into a cell and introduce the transformed cell into the animal under conditions favoring the propagation of the cell.

The transgene may also be introduced into the animal after birth. Five mice (three-weeks old) received an injection into its tail vein of a volume of 1 ml of tissue culture media containing $10^7$ particles of a replication-incompetent murine retrovirus bearing the PEPCK/bGH transcription unit. Four weeks later, serum samples exhibited a bGH concentration of 20-50 ng/ml.

This invention is not limited to any particular method of introducing the transgene into the animal.

Homozygous transgenic mouse lines are established by mating positive founder animals (positive offspring that result from the microinjected embryos) with normal mice of the same hybrid line. The F1 generation that is produced should be 50% heterozygous for the transgene if the transgene is contained in all of the germ cells of the founder. The heterozygous F1 animals are interbred and the F2 generation which is produced should be 25% homozygous for the transgene, 50% heterozygous, and 25% wild type. Therefore, by the F2 generation animals homozygous for the transgene can be produced; when these animals are bred with other homozygous mice the following generation is 100% homozygous at the transgene locus and a homozygous line has been established.

Founder mice were first screened for the presence of the exogenous PEPCK/bGH DNA by dot blot and Southern analysis. Mice which were positive by both these criteria (i.e., which exhibited the presence of the foreign gene and which yielded restriction fragments of the predicted length) were tested for expression of bGH by ELISA assay.

DNA was extracted from segments of the tail (about 1 cm), according to a modification of the procedure of Davis, et al., Meth. Enzymol., 65:404–411 (1980). Tail sections from potentially transgenic mice were crushed to a powder in liquid nitrogen. The dry powder was added to an extraction buffer which contained 100 ug.ml proteinase K, 0.5% SDS, 0.1 M NaCl, 50 mM Tris pH 7.5 and 1 mM EDTA, and then incubated overnight at 55° C. RNase T1 was added at a final concentration of 10 U/ml and the samples incubated 1 hour at 37° C. After RNase treatment, the DNA was extracted with a mixture which contained equal volumes of phenol and chloroform, then extracted with an equal volume of chloroform, and then ethanol precipitated.

The primary screening for positive transgenic animals was by DNA dot blot analysis. DNA extracted from the tails of mice was denatured in 0.1 M NaOH/2.0 M NaCl and applied to a nitrocellulose filter on a Schleicher and Schule manifold apparatus. A known amount of pPCbGH plasmid DNA was used as a standard for determining the copy number of the transgene. After the addition of the denatured DNA samples at 3 concentrations, the nitrocellulose filter was baked for 2 hours and prehybridized in a 50% formaide, 20 mM PIPES, 0.5% SDS solution containing 100 ug/ml denatured salmon testis DNA. The probe utilized for hybridization is shown in FIG. 6 (ECORI-BamHI PEPCK/bGH segment of pPCGH). This DNA fragment was labeled with $[a-^{32}P]$-dCTP by nick translation according to the procedure of Rigby, et al., J. Mol. Biol., 113:237–251 (1977). The copy number per haploid genome of the gene in positive, transgenic animals was determined by dot blot analysis. The dots were excised from the nitrocellulose after hybridization and autoradiography, and the hybridized radioactivity determined by liquid scintillation counting. The radioactivity hybridized to standard DNA samples increased linearly with amount spotted. Values of $3 \times 10^6$ kb of DNA per haploid mouse genome and 6.2 kb for pPCbGH were used in determining the copy number of the transgene in positive animals. The size of restriction fragment of the incorporated transgene was analyzed by Southern blotting, Southern, E. M., J. Mol. Biol., 98:503–517. The hybridizing probe (FIG. 6) was labeled either by nick translation Rigby, P. W. J., et al., J. Mol. Biol., 113: 237–251 (1977) or by random primer technique. Feinberg, A. P., et al, Anal. Biochem. 132:6–13 (1983).

Mice which were positive for both integration and expression of the chimeric PEPCK/bGH gene served as founder animals for the development of individuals transgenic lines.

Figure 2:
FIG. 2. Transgenic mouse bearing the PEPCK/bGH gene and litter-mate (white animal). The larger, black animal on the left contains, stably integrated into its genome, a chimeric PEPCK/bGH gene.
Figure 9:
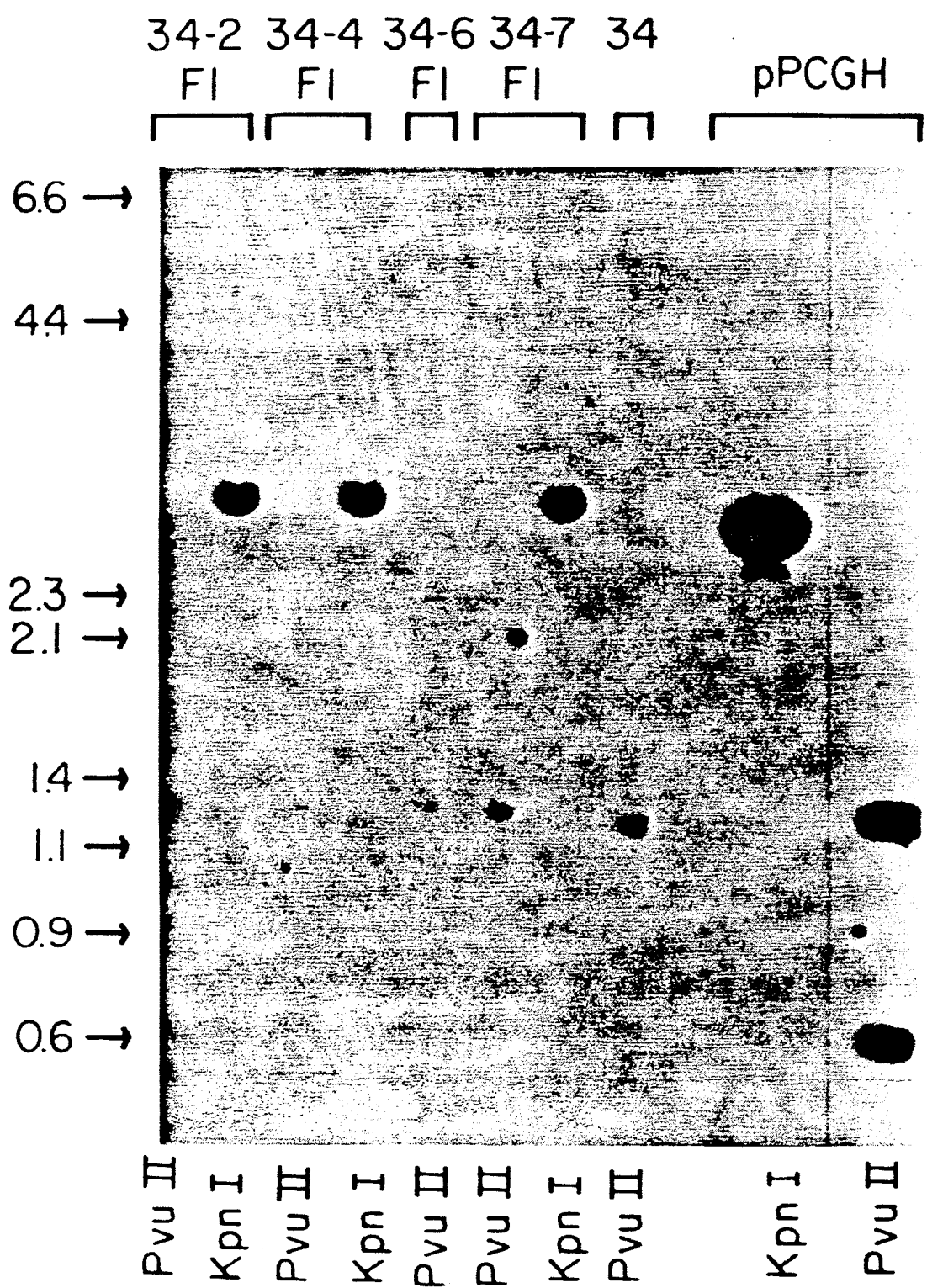
FIG. 9 Southern Blot Analysis of Mice Containing the PEPCK/bGH Transgene. Mouse DNA, extracted from tail biopsies, was digested with either Pvu II or Kpn I (as indicated). Mouse DNA was from founder #34, and offspring 34-2, 34-4, 34-6 and 34-7. Plasmid pPCGH was digested with Kpn I and Pvu II for control. Twenty ug of the restriction cut DNA was separated by electrophoresis and transferred to a nitrocellulose filter. The filter was hybridized with the Eco R1-Eco R1 PEPCK/bGH fragment labeled by nick translation.

Of 44 mice which were initially screened for the presence of the transgene, 2 were positive for integration (#9 and #34). Analysis of the DNA from these transgenic mice indicated that the PEPCK/bGH gene was integrated in a tandem head-to-tail repeat at single chromosomal loci in both founder animals. Digestion of the genomic DNA with Kpn I, an enzyme which cuts once within the gene, gave a fragment of the predicted length of approximately 2,700 bp, as indicated in FIG. 2, for founder #34 and offspring. Because the gene is present as a tandem, head-to-tail array, digestion with Kpn I resulted in multiple copies of a restriction fragment of the same length as the entire PEPCK/gGH gene, hybridized to the DNA probe (FIG. 9). Restriction enzyme digestion of genomic DNA with Pvu II, an enzyme which cuts the PEPCK/bGH gene at four sites, gave internal fragments in multiple copies of the predicted sizes of 1,300 bp, 635 bp and 355 pb (the smallest fragment is not distinguishable in FIG. 9). The Pvu II fragment created by the junction of the tandem head to tail array of the transgene was the same size as the 635 bp fragment. This same pattern with Kpn I and Pvu II was detected with all transgenic mice analyzed by Southern blot, indicating that there was no rearrangement, deletion or insertion within the transgene in the founders and their offspring.

Figure 10:
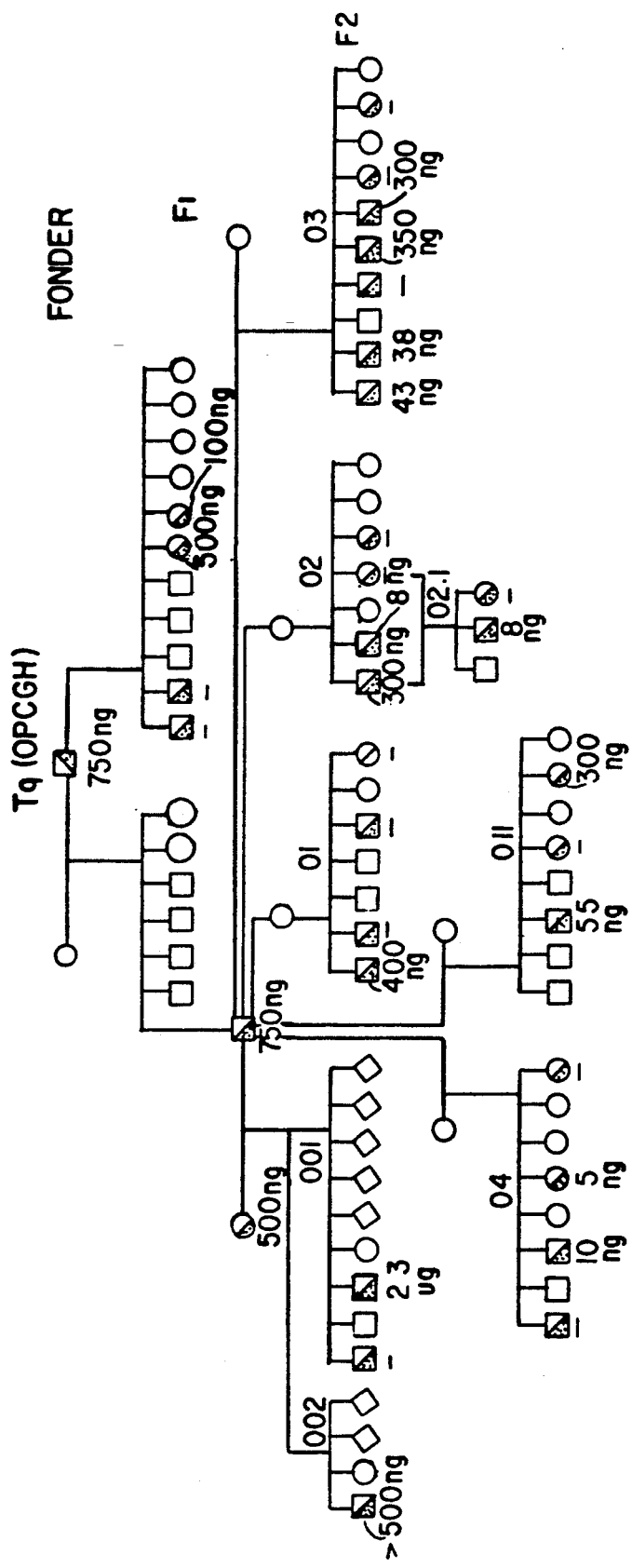
FIG. 10 Pedigree Illustrating Differential Transmission and Expression of the Chimeric PEPCK/bGH Gene from an F1 Male Expressing High Levels of bGH. Squares represent males, circles females, and diamonds animals which died prior to assay for integration of the transgene. Filled circles or squares represent animals which were heterozygous for the PEPCK/bGH gene as determined by dot blot analysis. Transgenic, male animals were either out-bred to C57BL6×SJL females or mated with heterozygous transgenic females as indicated. Serum bGH levels are expressed as ng of bGH/ml of serum. F1 and F2 litters are numbered for referral to Table 1. The heterozygous female from litter #2, expressing 500 ng bGH per ml of serum, is that shown in the mating between the heterozygous F1 male and female.

The copy number of the transgene in positive mice was determined by dot blot analysis. The first generation offspring of founder #9 exhibited different dot blot patterns; these ranged from 1-5 copies per cell to 25-50 copies per cell. First generation numbers of the gene, became the founders of individual lines. Matings between two heterozygous animals which are offspring of founder #9 (whose genomes contained 25 copies per cell) resulted in the death of a significant number of the offspring within a few days after birth (FIG. 10). This may indicate insertional mutagenesis in homozygous animals at a genetic locus important in development. The copy number in the founder #34 line was uniform, 25 copies per cell in the founder and F1 generation mice.

The ELISA (enzyme-linked immunosorbent assay) which we employ to determine the concentration of bGH in serum, involves the use of alkaline phosphatase streptavidin which binds to biotinylated goat anti-human IgG. The activity of the bound alkaline phosphatase can be measured by a colorimetry assay and therefore does not entail the use of radio-labeled ligands. Micro titer plates are initially coated with guinea pig anti-bGH, in excess such that it binds all bGH which is added in the samples to be assayed. Serum samples and purified bGH are added to the "coated" micro titer plates. A second antibody, monkey anti-bGH, is then added to bind quantitatively to in direct proportion to the amount of bGH bound to the first antibody. A third antibody, goat anti-human IgG (which recognizes monkey IgG) is chemically coupled to biotin so that the streptavidin-enzyme conjugate can be used as a detecting reagent; in this case the conjugate is alkaline phosphatase streptavidin. The bound alkaline phosphatase conjugate (which is bound to biotinylated goat anti-human IgG, in turn bound to monkey anti-bGH) is supplied with a substrate, and a colored product is generated. This product can then be measured spectrophotometrically. This enzyme reaction is linear over a long incubation period, which enhances the sensitivity of the assay method.

Microtiter plates were coated with guinea pig anti-bGH, diluted 1:100 in $Na_aCO_3/NaHCO_3$ (pH 9.6), incubated at 37° C. for 1 hour and then at 4° C. overnight. The plates were washed with 0.1% bovine serum albumin in phosphate buffered saline, (PBS) and "blocked" with 10% bovine serum albumin in PBS at 37° C. for 1 hour. Serum samples and standards containing known amounts of authentic bGH, diluted in 1% bovine serum albumin in PBS, were added, incubated at 37° C. for 1 hour and washed as described above. Monkey anti-bGH, diluted 1:10,000 in 1% bovine serum albumin in PBS, was added and incubated at 37° C. for 1 hour. Biotinylated goat anti-human IgG, diluted 1:2,000 in 1% bovine serum albumin in PBS, was added, incubated at 37° C. for 1 hour and washed as described above. The alkaline phosphatase-streptavidin conjugate, diluted 1:2,5000 in 1% bovine serum albumin in PBS, was added, incubated at 37° C. for 1 hour and washed as described above. The alkaline phosphatase-streptavidin conjugate, diluted 1:2,500 in 1% bovine serum albumin in PBS, was added, incubated at 37° C. for 1 hour and washed as described above. The alkaline phosphatase substrate, p-nitro-phenyl phosphate, diluted to 1 mg/ml in 1% bovine serum albumin in PBS, was added and incubated at 37° C. for 45 minutes to speed up color development. Plates were read in a Perkin-Elmer spectrophotometer at 1 hour and 5 hours.

We have determined that the cis acting elements of PEPCK gene, responsible for the specific expression of endogenous PEPCK in liver and kidney, are present within the 460 bp of 5'-flanking sequence which makes up the promoter/regulatory domain of the chimeric gene integrated within the genomes of these transgenic mice. In order to determine the tissue specificity of expression of PEPCK/bGH in these animals, the levels of RNA in various tissues was analyzed (FIG. 5).

RNA was extracted from mouse tissue essentially as described by Chirgwin, J. M., et al., Biochemistry, 24:5294-5299 (1979), with minor modifications Lamers, W. J., Proc. Natl. Acad. Sci. U.S.A. 79: 5137-5141 (1982). Total RNA (20 ug) was separated by electrophoresis on a 1% agarose, 18% formaldehyde gel with 20 mM MOPS, 5 mM Na acetate, 1 MM EDTA. The RNA samples were denatured at 80° C. for 5 minutes, in the above MOPS, 5 mM Na acetate, 1 mM EDTA. The RNA samples were denatured at 80° C. for 5 minutes, in the above MOPS, 5 mM Na acetate, 1 mM EDTA. The RNA samples were denatured at 80° C. for 5 minutes, in the above MOPS buffer, 3% formaldehyde and 0.1% SDS. The electrophoresis buffer was 20 mM MOPS, 5 mM Na acetate, 1 mM EDTA, 8.1% formaldehyde. After electrophoresis, the RNA was transferred directly to "Gene Screen Plus" in 20×SSC. When the transfer was complete, the RNA was crosslinked to the "Gene Screen Plus" membrane by exposure to ultra violet light for approximately 3 minutes and then baked for 2 hours at 80° C. The RNA was hybridized to a nick translated ($1 \times 10^6$ cpm/ml) Eco R1 fragment of the pPCbGH chimeric gene, shown in FIG. 6. Both the prehybridization and hybridization solutions consisted of 50% formalmide, 0.2 M NaCl, 50 mM Tris pH 7.5, 10% dextran sulfate, 0.1 sodium pyrophosphate, 1% SDS, 0.2% bovine serum albumin, 0.2% Ficoll (mw 400,000), 0.2% PVP (mw 40,000) and 0.1 mg/ml salmon testis DNA. After hybridization for 36 hours, the filters were washed twice with 2×SSC, 0.1% SDS for 5 minutes at room temperature, followed by two washings with 2×SSC, 0.1% SDS for 30 minutes at 42° C.

The mature RNA transcript of the PEPCK/bGH gene (including the 73 bp of the first exon of PEPCK) is approximately 1 kb whereas the mRNA for the endogenous PEPCK gene is approximately 2.8 kb. Cimbala, M. A., J., et al., Biol. Chem. 257: 7629-7636 (1982). The probe utilized for Northern analysis hybridizes with both the chimeric PEPCK/bGH and endogenous PEPCK.

Figure 5:
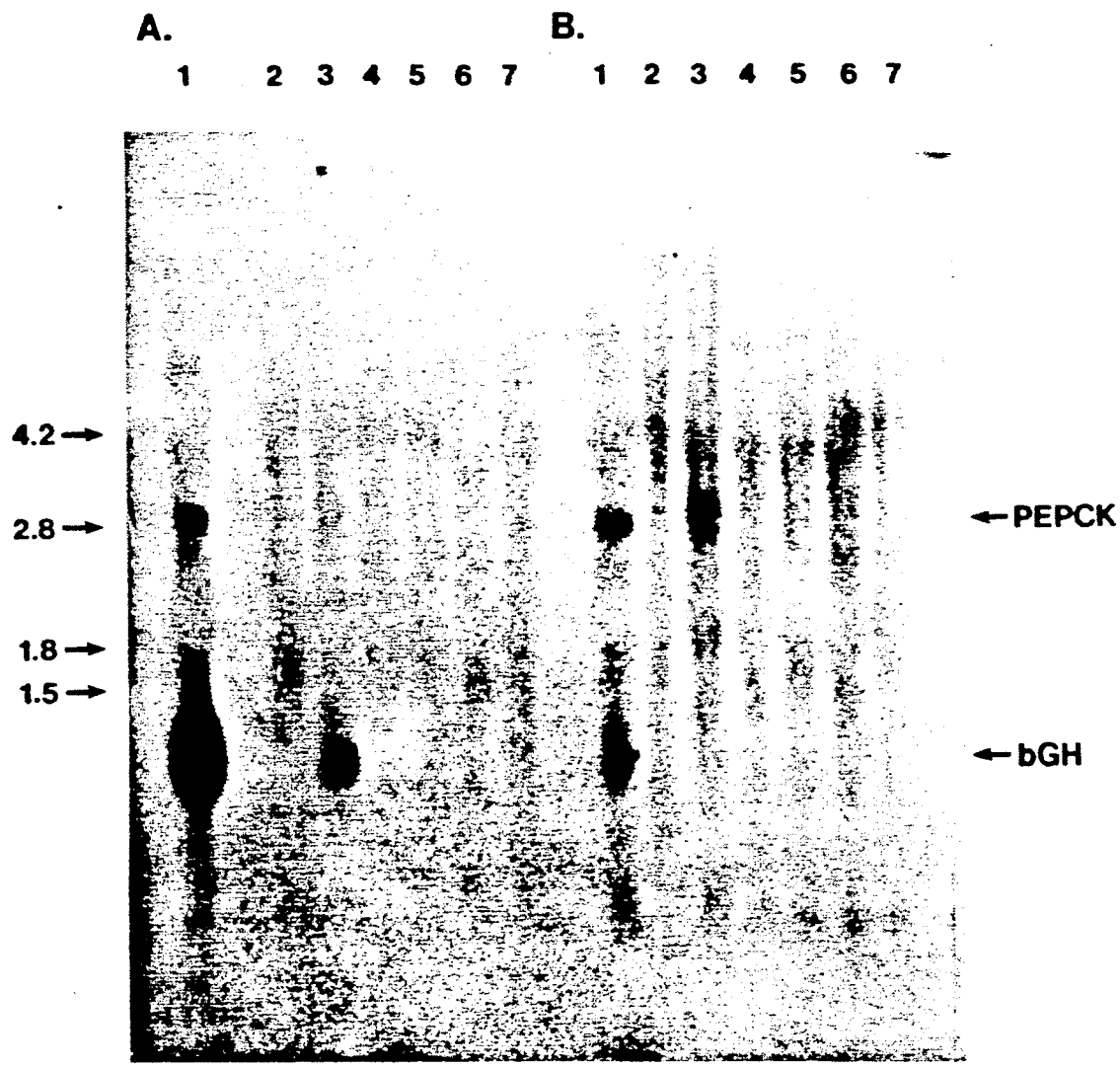
FIG. 5. Tissue specific expression of the bovine growth hormone mRNA in transgenic mice containing the PEPCK/bGH gene. Analysis of bGH mRNA by Northern blotting using as a probe a segment of DNA containing the PEPCK promoter and bGH structural gene (Eco RI/Eco RI fragment) shown in FIG. 6. Each lane contains 30 ug of total RNA extracted from various tissues, taken from transgenic mice. The mRNA produced by the chimeric PEPCK /bGH gene contains 73 bp of PEPCK mRNA and 1.0 kb of RNA coding for bGH. The position of both mRNA species is indicated directly on the figure, together with molecular size markers. Panel A. Transgenic mouse which expresses high levels of bGH (750 ng/ml of serum) lanes 1–7, 1, liver; 2, spleen; 3, kidney; 4, heart; 5, lung; 6, brain; 7, intestine. Panel B. Transgenic mouse which expresses low levels of bGH (10 ng/ml of serum). Lanes 1–7 are the same as in Panel A.

As indicated in FIG. 5, when transgenic animals containing serum bGH were tested for the tissue specificity of this expression, they showed high levels of expression in liver. As shown in FIG. 5 panel A and B (lane 1), there is an intense band at 1.0 kb which hybridized to the pPCbGH probe. The transgene was also expressed in the kidney of the mouse in panel A; the kidney is another tissue in which endogenous PEPCK is expressed. No detectable PEPCK/bGH mRNA was found in the kidney of the animal in panel B, which expressed low levels of bGH, due possibly to limitations in the sensitivity of the Northern analysis. However, expression of the transgene in the kidneys of low expressing animals has been detected using a bovine growth hormone cDNA probe labeled by random priming.

Figure 3:
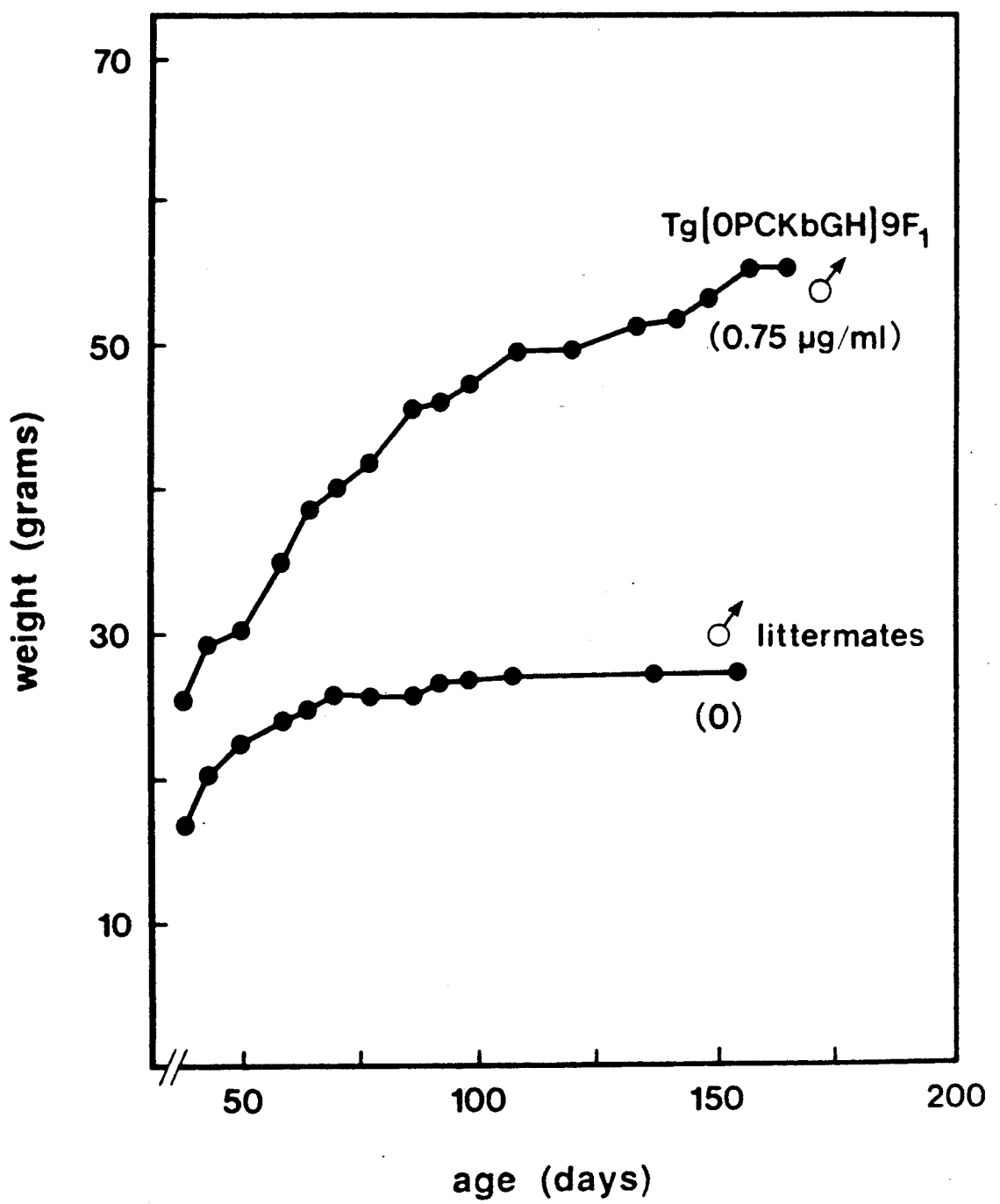
FIG. 3. Growth rate of the mouse containing the PEPCK/bGH transgene. The animal shown in FIG. 2 TG[OPCKbGH]9F1 expresses bovine growth hormone at 0.75 mg/ml of serum and has grown to be twice the size of its litter-mates.

Based on these findings we conclude that the sequences which are required for expression in liver and kidney are present in the 460 bp PEPCK fragment and the chromosomal site of integration of the chimeric PEPCK/bGH gene in this individual heterozygous mouse line does not interfere with tissue specific expression of the transgene. When mice of a separate lineage, which contained the gene but did not exhibit measurable serum bGH levels, were assayed for bGH specific mRNA, there was no bGH mRNA in any of the tissues examined. Transgenic mice which expressed high levels of bGH were approximately 1.5 to 2 times the size of their litter-mates of the same sex (FIG. 3 and Table 1). This indicates that the growth hormone produced by these animals was biologically active and processed correctly in the ectopic sites, the liver and kidney, in which it was produced.

Table I: Properties of Transgenic Mice Containing the PEPCK/bGH Gene. The copies of PEPCK/bGH per haploid genome were determined by dot blot; the plasmid pPCGH was used for the copy number standard at copy number equivalents of 1,5,10,15,25,50 and 100. For quantitative, dots were excised from nitrocellulose filters after hybridization and autoradiography, and the amount of the probe hybridized determined by liquid scintillation counting. The concentration of bGH in the serum were determine as described in the Materials and Methods. The growth ratio is calculated by dividing the weight of the transgenic mouse by the average weights of littermates of the same sex.

TABLE I

| Mouse | Sex | PEPCK/bGH copies/cell | bGH ng/ml serum | Growth Ratio |
|---|---|---|---|---|
| 9 | M | 25 | 1,000 | 1.5 |
| 34 | F | 25 | 25 | 1.0 |
| 1-1 | M | 25 | 1,000 | 2.0 |
| 2-1 | M | 5 | 0 | 1.0 |
| 2-2 | M | 5 | 0 | 1.0 |
| 2-6 | F | 25 | 500 | 1.7 |
| 2-7 | F | 5 | 100 | 1.0 |
| 001-1 | M | 25 | 0 | 1.0 |
| 001-3 | M | 50 | 2,300 | 1.5 |
| 002-1 | M | 25 | 500 | 1.6 |
| 01-1 | M | 25 | 400 | 1.3 |
| 01-2 | M | 25 | 0 | 1.0 |
| 01-5 | M | 25 | 0 | 1.0 |
| 01-7 | F | 25 | 0 | 1.0 |
| 02-1 | M | 25 | 300 | 1.4 |
| 02-2 | M | 25 | 8 | 1.0 |
| 02-4 | F | 25 | 0 | 1.0 |
| 02-5 | F | 25 | 0 | 1.0 |
| 03-1 | M | 25 | 43 | 1.0 |
| 03-2 | M | 25 | 38 | 1.0 |
| 03-4 | M | 25 | 0 | 1.0 |
| 03-5 | M | 25 | 350 | 1.4 |
| 03-6 | M | 25 | 300 | 1.5 |
| 03-7 | F | 25 | 0 | 1.0 |

An alternative splicing mechanism for bGH RNA is known to take place in bovine pituitary tissue, Hampson, R. K., et al., Proc. Natl. Acad. Sci., USA 84:2673-2677 (1987). A low percentage (0.1%) of bGH mRNA contains intron D of bGH gene. The inclusion of intron D which continues as an altered, open reading frame through the first 50 nucleotides of exon 5. The physiological significance of this altered gene product is not known. When the total RNA from several different tissues of a transgenic mouse was hybridized with a probe consisting of bGH intron D sequence alone, a band of 1.3 kb RNA was detected in liver only. Thus, this alternative process of bGH RNA splicing also takes place in transgenic mice but is not specific for the pituitary gland, since it also occurs in the livers of these transgenic mice.

Marked alterations in the level of expression of the chimeric PEPCK/bGH gene in these animals were caused by dietary changes. The two synthetic diets used in this study were purchased from Nutritional Biochemical Corporation. The high carbohydrate diet contained 81.5% sucrose, 12.2% casein, 0.3% DL-methionine, 4% cottonseed oil, 2% brewers yeast and a 1% mineral mix plus vitamins. The high protein diet contained 64% casein, 22% a-cell nutritive fiber, 11% vegetable oil, 2% brewers yeast and a 1% mineral mix with vitamins. The mice were fed these diets and water on a ad libitum basis.

Figure 4:
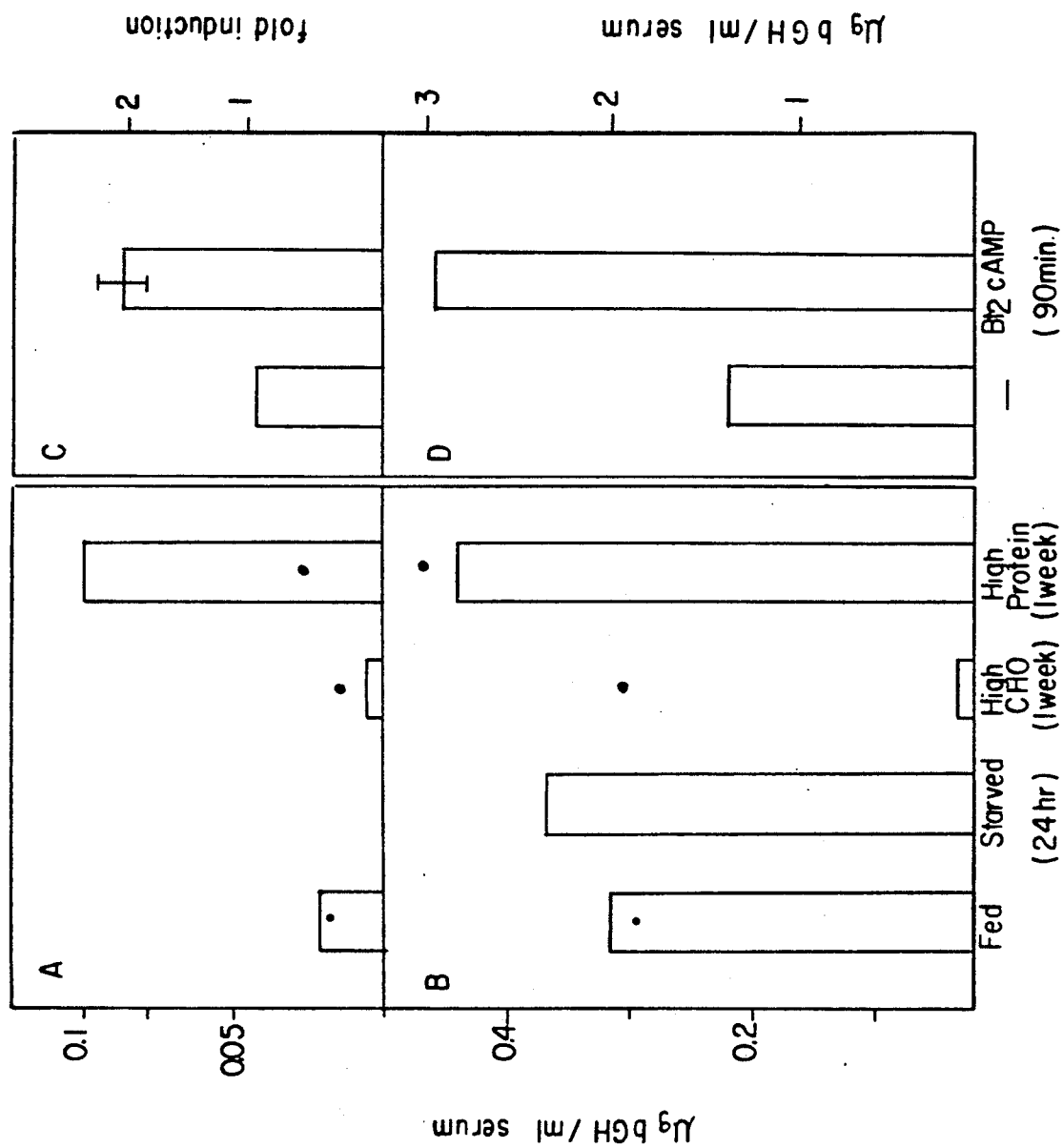
FIG. 4. Effect of High Carbohydrate and High Protein Diets and $Bt_2$ cAMP Administration on the Levels of bGH in the Serum in Transgenic Mice. Panel A—A representative transgenic mouse, expressing low levels of serum bGH was placed on a high carbohydrate diet for 1 week. The animal was then fed a high protein diet devoid of carbohydrate for 1 week. Blood was drawn from the tail vein at the time intervals indicated and the levels of bGH in the serum determined. Panel B—A representative transgenic mouse, expressing high levels of serum bGH, was starved for 24 hours and then fed a high carbohydrate diet for 1 week. The animal was then fed a high protein diet devoid of carbohydrate for 1 week, as described in Panel A. Panel C—Four transgenic mice, expressing bGH at serum concentrations ranging from 2.4 ng/ml to 1.4 ug/ml, were injected with $Bt_2$cAMP and theophylline (both 30 mg/kg) at 3 consecutive 30 min intervals. After 90 minutes the mice were bled from the tail vein and the concentration of bGH in the serum determined. Changes in the levels of bGH in the serum are expressed as a "fold increase." Panel D—A transgenic mouse was treated as described in Panel C and the alteration in the concentration of serum bGH determined.

Transgenic animals were fasted for 24 hours and then placed on a high carbohydrate (81.5%), minimum protein (12.5%) diet. After one week on this diet, the level of bGH in the serum of a representative animals dropped from a basal value of 320 ng bGH/ml serum to 14 ng bGH/ml serum. When the high carbohydrate diet was replaced with a high protein (61%), carbohydrate-free diet, the serum bGH levels rose from 14 ng bGH/ml to 430 ng/ml after one week (FIG. 4). Transgenic animals which expressed bGH at lower levels exhibited the same pattern of expression correlated with these alterations in diet.

Diets high in carbohydrate markedly depress the synthesis of PEPCK by increasing the level of insulin in the serum, which in turn inhibits gene transcription Granner, D., et al., Nature 305:549-551 (1983). The half-life of PEPCK mRNA is only 30 minutes (44,45) so that a decrease in the level of specific mRNA synthesis after a meal high in carbohydrate results in a rapid drop in hepatic PEPCK synthesis. Conversely, starvation or a diet devoid of carbohydrate, but high in protein, will induce the activity of PEPCK in the liver.

After 7 days of a high-carbohydrate diet, the levels of bGH in the blood of the transgenic mice tested were reduced to less than 5% of that found in the same animals after 24 hours of starvation. Subsequent refeeding of a diet containing 64% protein resulted in a 30-fold induction of serum bGH after only 7 days. This marked and relatively rapid response of the PEPCK/bGH transgene to changes in the dietary status of the host animal indicates that the PEPCK promoter/regulatory region offers an effective means of targeting a linked structural gene for expression in the liver, which could be regulated by simply changing the diet of the animal.

In order to determine whether the cAMP regulatory domain present in the 460 bp of PEPCK promoter included in the PEPCK/bGH gene, functions in transgenic mice, animals were injected intraperitoneally at three 30 minute intervals with $Bt_2$ cAMP and theophylline. At 90 minutes blood was drawn from the tail vein of the animal and the serum tested for bGH. Serum levels of bGH were increased 2 to 3-fold within 90 minutes following the first cAMP injection (FIG. 4). Animals which were positive for integration of the transgene, but negative for its expression were not induced to express bGH by the administration of Bt₂cAMP. Thus, transgenic animals bearing the chimeric PEPCK/bGH gene, which express bGH, contain the cis acting sequences required for the regulation of its expression by cAMP.

The rapidity of the response of the PEPCK/bGh gene in the transgenic animals to the administration of Bt₂cAMP is also predicted from the previous studies in which we have demonstrate that this cyclic nucleotide will induce the transcription of the PEPCK gene in the livers of rats by 8-fold within 20 minutes, Lamers, W. J., et al., Proc. Natl. Acad. Sci. U.S.A., 79:5137-5141 (1982). The segment of the PEPCK promoter/regulatory region used to construct the chimeric PEPCK/bGH chimeric gene (−450/+73) contains a cAMP regulatory element in the region between −109/−79, Short, J. M., et al., Biol. Chem. 261: 9721-9726 (1986). This element contains the core sequence CTTACGTCAGAGG which is also present in the promoter/regulatory region of the gene for cytosolic PEPCK for the chicken Hod, Y., et al., J. Biol. Chem. 259:15609-15614 (1984). This regulatory element has been shown to confer cAMP sensitivity on a heterologous gene containing its own promoter and to function in a variety of cell types into which it was introduced by either transfection, Short, J. M., et al., Biol. Chem. 261:9721-9726 (1986) or by infection with a retrovirus. Our findings indicate that the transgene is integrated into the host DNA in a manner which preservers not only its tissue-specific expression, but also the ability of the gene to be regulated by the same hormones which control the expression of the native gene in the normal chromosomal location.

Different patterns of integration and expression of the chimeric PEPCK/bGH gene was observed in the lines of transgenic mice. Founder animal #34, which expressed bGH at approximately 25 ng/ml serum, transmitted the gene to progeny in the predicted Mendelian ratios, consistent with the presence of the transgene in all of the germ cells of the founder. However, the progeny, while containing the equivalent number of copies as the founder animal, did not express detectable levels of bGH. This has also been reported for other genes in transgenic animals. Palmiter, R. D., et al., Cell 29:701-710 (1982). Founder animal #9, which was positive for integration and expression of the PEPCK/bGH gene, was mosaic. Significantly less than 50% of the progeny of this founder animal contained the transgene and of those positive for the gene, some expressed it whereas others did not. When two F1 animals (offspring of founder #9), heterozygous for, but not expressing the transgene, were mated, homozygous animals were produced which did express bGH (data not shown). From founder mouse #9, F1 animals were produced which expressed high levels of bGH (300-2,300 ng/ml serum), medium levels (40-100 ng/ml serum) and low levels of bGH (1-10 ng/ml serum). The level of expression of the gene was not strictly correlated with copy number (Table I).

A segment of one transgenic line is depicted as a pedigree in FIG. 10. As indicated, the founder animal Tg[OPCGH]9 (#9) was genetically mosaic and expressed bGH at high levels. One F1 male with high levels of expression and a 2-fold increase in growth was chosen to initiate a transgenic line of animals which expressed high levels of growth hormone. The PEPCK/bGH gene is transmitted from the high expressor F1 male in a Mendelian fashion to the F2 generation. However, not all of the animals which contain the transgene express bGH and those that do, express it at varying levels although the copy numbers are the same. Also notable is the fact that significantly more males of the F2 generation than females (11 out of 25 transgenic males vs. 1 out of 21 transgenic females, in 12 litters tested) expressed the gene at high levels, although females have integrated within their genomes an equal number of copies of the gene.

The acute responsiveness of the PEPCK promoter/regulatory region to induction by diet and hormones and its tissue-specific expression in the liver and kidney make it an ideal tool for targeting various structural genes of interest to these tissues. It is also possible to modulate the level of expression of the structural gene over a broad range by altering the carbohydrate content of the diet of the transgenic animal. Since PEPCK gene is normally not expressed until birth, the developing fetus is not exposed to a high level of protein from the linked structural gene. This has clear advantages with hormones such as GH, which have the potential of interfering with the normal development of the fetus. We have noted normal reproductive capacity of the animals which were generated from this initial series of experiments. It should also be possible to use the tissue specific element in the PEPCK regulon to direct the expression of a heterologous gene, containing its own promoter, to the liver.

Transgenic mice expressing high levels of bGH (0.5-2.3 ug/ml of serum) grew to twice the size of their littermates who did not express the transgene (see growth curve in FIG. 3). Despite this altered pattern of growth, these animals were in good health and were reproductively active. We did notice, however, that mice with both high and low levels of expression of the bGH gene were more sensitive to the administration of insulin than were mice not expressing the chimeric PEPCK/bGH gene. Mice which contained the transgene, but did not express it, were no more sensitive to insulin than normal, control animals. The administration of low concentration of insulin (0.05 U/kg) to transgenic animals was lethal in the absence of glucose gavage.

In order to produce transgenic swine with a phenotype mimicking the performance traits of swine injected with the growth hormone protein, approximately 400 copies of a 2.8 kilobase (kb) linear fragment containing the PEPCK-bGH gene were injected into the pronuclei of fertilized swine eggs. One thousand and fifty seven (1057) eggs were injected and transferred to 33 synchronized foster sows; 22 of the sows retained their pregnancy and 112 injected eggs resulted in live born neonates.

The approximate number of integrated PEPCK-bGH gene sequences in these animals was determined by dot hybridization and positive animals were demonstrated to contain the integrated sequences with copy numbers ranging from 1 to 200 copies per cell. Seventeen transgenic animals showed significant levels of bovine growth hormone protein in their circulating serum, with concentrations ranging from 5 ng/ml to 200 ng/ml, as determined by radioimmune and ELISA assays. A detailed analysis of the integration and expression of the bGH gene in two of these animals (#11 and #44) is presented here.

Genomic DNA extracted from the tails of pigs was digested with Eco R1, Kpn 1, Pst I and Pvu II. The digested DNA was hybridized with the Bam HI-Bgl II fragment from −547 to +73 of the rat PEPCK gene, labeled by "random priming." Eco R1 digestion of the genomic DNA yielded a 2.8 kb fragment which hybridized with the above probe, indicating that the transgene was present as a tandem repeat integrated within the host genome in pigs #11 and #44. There are four internal Pvu II sites within the transgene; three of these should hybridize with the Bam-HI-Bgl II probe. The predicted internal fragments of 740 bp and 520 bp were observed in genomic DNA from both animals. A third fragment which spans the junction between the tandem repeats is the same size as the 740 bp internal fragment. In both animals the transgene is present as a tandem repeat in which some of the copies of the gene are inverted, as indicated by the restriction fragments generated after digestion with Kpn I and Pst I. A head to tail, tail to head repeat of the transgene should yield a 5.0 kb fragment after digestion to head repeat of the transgene should yield a 5.0 kb fragment after digestion with Kpn I, which should hybridize with the Bam HI-Bgl II DNA probe in two positions. Genomic DNA from both pig #11 and pig #44, when digested with Kpn I, yielded a 5.0 kb fragment. Digestion with Pst I should yield a 1.2 kb fragment which hybridizes with the probe at two positions when the transgene is inverted. DNA from pig #44 yielded a 1.2 kb fragment upon Pst 1 digestion, which is consistent with the presence of adjacent head to head repeats. The 1.7 kb fragment is an endogenous PEPCK fragment which hybridizes with the Bam HI-Bgl II probe. When DNA from pig #11 was digested with Pst I we noted a 1.7 kb fragment, but not the 1.2 kb fragment observed in pig #44. In addition, there was also a fragment of 4.0 kb in this animal; this may indicate the deletion of Pst I sites in copies of the transgene within this animal.

While detailed tissue specific expression analysis at the mRNA level could not be performed on pig #11 or other transgenic swine because of our desire to retain their viability for performance and breeding studies, pig #44 was sacrificed for this purpose.

RNA isolated from the liver, kidney, lung, spleen and intestine of pig #44 was subjected to S1 nuclease digestion after hybridization with a 5'-end labeled fragment of DNA generated by restriction endonuclease digestion of PEPCK/bGH gene with BamHl and Pst I. In addition, RNA from a transgenic mouse containing the same PEPCK/bGH chimeric gene, and expressing bGH at levels >500 ng/ml serum, was analyzed. A 133 bp fragment of the Bam Hl-Pst I probe was protected from nuclease digestion by RNA from pig liver, but not by RNA from any of the other pig tissues examined. Thus, the 460 bp of 5'-flanking sequence from the PEPCK gene can direct the tissue specific expression of the linked bGH structural gene in a transgenic pig. PEPCK is expressed primarily in the liver and kidney cortex in mammalian species; however, PEPCK/bGH mRNA could be detected only in the liver of pig #44. By comparison, in the transgenic mouse, that mRNA is present in both liver and kidney, although the ratio of liver to kidney mRNA is much lower than is observed for endogenous PEPCK mRNA, Meisner, H., et al., Biochemistry 224:412-425 (1985). This may indicate that further sequences outside of the Eco R1-Bgl II fragment are required for full expression of the transgene in the kidney. S1 nuclease analysis also indicates that the PEPCK/bGH chimeric gene in the pig uses the correct start site of transcription, since the predicted size fragment (133 bp) is protected.

Pig #11, shown by duplicate radioimmune and ELISA assays to contain 200 ng/ml of bGH in his serum, was placed on a similar feed regimen compared to his non-transgenic male littermate (#12). Feed:-weight gain ratios and back fat measurements were compared. The feed:gain ratio was significantly reduced in PEPCK-bGH transgenic pig #11 as compared to the non-transgenic control (30% decrease during restricted feeding conditions. Pigs #11 and 12 were compared during two consecutive periods of approximately 45 days each. Animals were fed a 16% crude protein commercial finishing ration during both periods. Pigs were 125 days old and weighed between 50 and 75 kg when the ad libitum feeding period began (period 1). Animals were restricted to 2.8 kg of feed per day during the second period.

TABLE 2

| | Ad-libitum Feeding | | Restricted Feeding | |
|---|---|---|---|---|
| | Pig #11 | Pig #12 | Pig #11 | Pig #12 |
| Avg Daily Gain (Kg) | 1.0 | 1.2 | .8 | .5 |
| Feed:Gain | 3.8 | 4.3 | 3.5 | 5.3 |

The most remarkable observation was the dramatic reduction in body fat in pig #11 as compared to control. In FIG. 11C, the data clearly shows that the transgenic pig (#11) has accumulated less than ½ the back fat that has built up on his littermate control over the same feeding regimen. These results compare favorably with the observed changes in growth and carcass composition in pigs administered exogenous growth hormone, Chung, C. S., et al., J. Animal Science 60:118-130 (1985); Etherton, T. D., et al., J. Animal Science 63:1389-1399 (1986); Machlin, L. J., J. Animal Science 35:794-799 (1972). No pathology or infirmity was observed the PEPCK-bGH transgenic swine #11 from birth through maturity. The animal also showed normal libido and appeared to be reproductively sound.

These experiments demonstrate that, when appropriately regulated, genes transferred into the germline of agricultural animals can have a profound and positive effect on animal performance and the economics of animal husbandry. During the last several years, studies in mice have proven that transgene expression may be regulated as to the time and tissue of choice, Palmiter, R. D., et al., Cell 41:343-345 (1985). Application of these principles, through the use of the PEPCK promoter/regulatory element, has resulted in the production of lines of transgenic swine with increased economic efficiency (feed:gain ratios) which produce a leaner meat product. This may provide a positive influence on the health of the consumer of pork products, since the U.S. National Academy of Science has recently reported that the consumption of excessive animal fat is the most significant contributor to diet-related disease in the U.S. Call, D. L., et al., Designing Foods: Animal Product Options in the Marketplace, National Research Council 18-62, (1988).

We claim;

1. A method of introducing a gene into the liver cells of a mammal in utero which comprises providing a retroviral vector bearing an expressible gene which is foreign to an individual recipient fetal mammal and operably linked to a liver-specific promoter, injecting the vector into the peritoneal cavity of said mammal while it is in a fetal stage of development, and permitting development of said mammal from the fetal stage, during which development the vector is transported to the fetal liver, infects endogenous hemopoietic cells of said fetal liver, and integrates into the genome of said cells conferring on said infected cells the ability to express said gene.

2. The method of claim 1 in which the gene is operably linked to a PEPCK promoter.